(12) United States Patent
Callaghan et al.

(10) Patent No.: US 10,688,236 B2
(45) Date of Patent: Jun. 23, 2020

(54) SYSTEMS AND METHODS FOR PERFORMING MEDICAL PROCEDURES INVOLVING ACCESSING THE LYMPHATIC SYSTEM

(71) Applicants: Matthew J. Callaghan, Stanford, CA (US); Christian S. Eversull, Palo Alto, CA (US); Stephen A. Leeflang, Sunnyvale, CA (US)

(72) Inventors: Matthew J. Callaghan, Stanford, CA (US); Christian S. Eversull, Palo Alto, CA (US); Stephen A. Leeflang, Sunnyvale, CA (US)

(73) Assignee: LXS, LLC, Palo Alto, CA (US)

( * ) Notice: Subject to any disclaimer, the term of this patent is extended or adjusted under 35 U.S.C. 154(b) by 454 days.

(21) Appl. No.: 14/444,999

(22) Filed: Jul. 28, 2014

(65) Prior Publication Data

US 2014/0358071 A1    Dec. 4, 2014

Related U.S. Application Data

(63) Continuation-in-part of application No. 14/160,547, filed on Jan. 21, 2014, now Pat. No. 10,111,997, and
(Continued)

(51) Int. Cl.
*A61M 1/34*    (2006.01)
*A61M 1/36*    (2006.01)

(52) U.S. Cl.
CPC .......... *A61M 1/3496* (2013.01); *A61M 1/367* (2013.01); *A61M 1/3609* (2014.02);
(Continued)

(58) Field of Classification Search
CPC .............. A61M 1/3496; A61M 1/3609; A61M 1/3653; A61M 1/367; A61M 2230/208;
(Continued)

(56) References Cited

U.S. PATENT DOCUMENTS 4,316,466 A * 2/1982 Babb .................. A61M 1/0005
604/31
4,957,484 A * 9/1990 Murtfeldt .......... A61M 25/0074
604/102.02
(Continued)

OTHER PUBLICATIONS

Pflug, J. and J. Calnan, The Valves of the Thoracic Duct at the Angulus Venosus, Brit J. Surg, 1968, vol. 55, No. 12, Dec., 6 pages.

*Primary Examiner* — Bhisma Mehta
*Assistant Examiner* — Hamza A Darb
(74) *Attorney, Agent, or Firm* — William A. English; Vista IP Law Group LLP

(57) ABSTRACT

System and methods are provided for harvesting one or more organs, e.g., a lung from a donor body. In one embodiment, a distal end of a tubular member is introduced into the donor body's vasculature via a percutaneous access site, and the tubular member is manipulated until the distal end of the tubular member is disposed within the thoracic duct. Fluid is removed from the thoracic duct through the tubular member to a location exterior to the patient's body, and one or more organs are removed from the donor body. Optionally, one or more parameters within the thoracic duct or other parameters of the donor body may be monitored and fluid removal may be adjusted to reduce fluid accumulation within the one or more organs.

24 Claims, 8 Drawing Sheets

Related U.S. Application Data a continuation-in-part of application No. 14/214,882, filed on Mar. 15, 2014, now Pat. No. 10,052,059, application No. 14/444,999, which is a continuation-in-part of application No. 14/300,179, filed on Jun. 9, 2014.

(60) Provisional application No. 61/859,175, filed on Jul. 27, 2013, provisional application No. 61/754,911, filed on Jan. 21, 2013, provisional application No. 61/800,161, filed on Mar. 15, 2013, provisional application No. 61/832,820, filed on Jun. 8, 2013.

(52) U.S. Cl.
CPC ... *A61M 1/3653* (2013.01); *A61M 2202/0405* (2013.01); *A61M 2205/3306* (2013.01); *A61M 2205/3317* (2013.01); *A61M 2230/207* (2013.01); *A61M 2230/208* (2013.01)

(58) Field of Classification Search
CPC .. A61M 2205/3317; A61M 2205/3306; A61M 2230/207; A61M 2202/0405; A61M 1/0096; A61M 1/0098; A61M 1/0008; A61M 1/0023
See application file for complete search history.

(56) References Cited

U.S. PATENT DOCUMENTS

| | | |
|---|---|---|
| 5,300,022 A | 4/1994 | Klapper et al. |
| 5,391,143 A | 2/1995 | Kensey |
| 5,766,151 A | 6/1998 | Valley et al. |
| 6,443,925 B1 | 9/2002 | Schaible et al. |
| 6,547,775 B1 | 4/2003 | Blyakhman |
| 2006/0100658 A1 | 5/2006 | Obana et al. |
| 2007/0032754 A1 | 2/2007 | Walsh |
| 2007/0282382 A1 | 12/2007 | Shuros et al. |
| 2008/0004597 A1 | 1/2008 | Lattouf et al. |
| 2008/0009719 A1 | 1/2008 | Shuros et al. |
| 2008/0097412 A1 | 4/2008 | Shuros et al. |
| 2008/0140000 A1 | 6/2008 | Shuros et al. |
| 2009/0054805 A1 | 2/2009 | Boyle |
| 2009/0197240 A1* | 8/2009 | Fishman .................. A01N 1/02 435/1.2 |
| 2010/0217346 A1 | 8/2010 | Shuros |
| 2011/0276023 A1 | 11/2011 | Leeflang et al. |
| 2012/0029466 A1 | 2/2012 | Callaghan et al. |
| 2012/0330132 A1 | 12/2012 | Sorajja et al. |
| 2013/0245607 A1 | 9/2013 | Eversull et al. |
| 2014/0243790 A1 | 8/2014 | Callaghan et al. |
| 2014/0303461 A1 | 10/2014 | Callaghan et al. |
| 2014/0364765 A1 | 12/2014 | Callaghan et al. |

\* cited by examiner

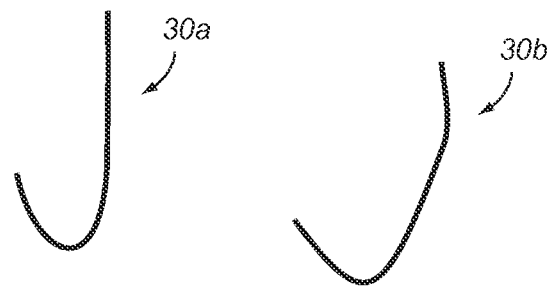
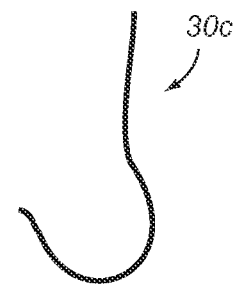
FIG. 3A
FIG. 3B
FIG. 3C
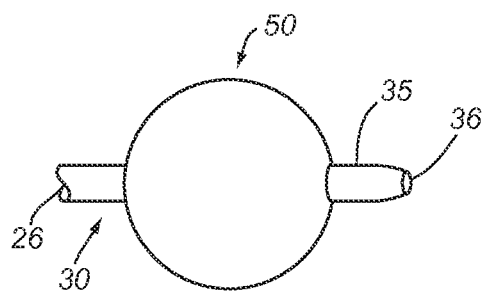
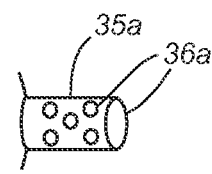
FIG. 4A
FIG. 4B
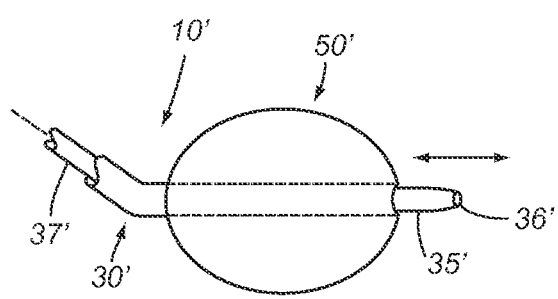
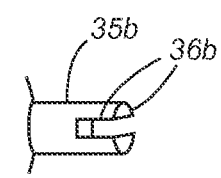
FIG. 4D
FIG. 4C

SYSTEMS AND METHODS FOR PERFORMING MEDICAL PROCEDURES INVOLVING ACCESSING THE LYMPHATIC SYSTEM

This application claims benefit of co-pending provisional application Ser. No. 61/859,175, filed Jul. 27, 2013, and is a continuation-in-part of co-pending application Ser. No. 14/160,547, filed Jan. 21, 2014, which claims benefit of provisional application Ser. No. 61/754,911, filed Jan. 21, 2013, Ser. No. 14/214,882, filed Mar. 15, 2014, which claims benefit of provisional application Ser. No. 61/800, 161, filed Mar. 15, 2013, and Ser. No. 14/300,179, filed Jun. 9, 2014, which claims benefit of provisional application Ser. No. 61/832,820, filed Jun. 8, 2013. The entire disclosures of these applications are expressly incorporated by reference herein.

FIELD OF THE INVENTION

The present invention relates generally to apparatus and methods used to perform medical procedures, and, more particularly, to systems and methods for performing medical procedures that include accessing and/or otherwise involving the lymphatic system of a patient, e.g., to facilitate lung or other organ transplantation.

BACKGROUND

Only about ten to fifteen percent (10-15%) of multi-organ donors have lungs that are suitable for transplantation and the resulting organ shortage is a well-known problem. Pulmonary edema contributes to donor organ inviability and may be caused by an increase in vascular pressure or an increase in capillary permeability. Vascular pressure increases are the result of pump failure (cardiogenic), volume infusion, and vasopressor use to maintain hemodynamic stability and organ perfusion. Increased capillary permeability is due to the release of inflammatory mediators and is well documented in brain death.

The lymphatic system includes a network of vessels generally separate from veins and arteries. Rather than whole blood, the lymphatic vessels carry lymphatic fluid (or lymph). The lymphatic system serves a variety of physiologic purposes, including returning interstitial fluid to the vascular space, transporting fats from the digestive tract, and transporting immune-mediating cells. The composition of lymphatic fluid is similar to plasma. It contains white blood cells, but generally does not contain red blood cells, platelets, or various other components of whole blood. The lymphatic system culminates in a single large channel called the thoracic duct, which joins the central venous system at the confluence of the left internal jugular and subclavian veins.

Historically, the lymphatic system has been directly accessed rarely in medical procedures. For example, some diagnostic procedures involve direct cannulation of peripheral lymphatic vessels, e.g., to infuse dye for identification of lymph nodes. Direct access of the central lymphatic vessels, such as the thoracic duct, is generally avoided. For example, a defect created in the thoracic duct generally does not readily close on its own, leading to significantly morbid conditions, such as chylothorax (persistent collection of lymphatic fluid around the lungs).

The lymphatic system does, however, eventually drain into the vasculature. A majority of lymphatic vessels come to a confluence in the thoracic duct which generally enters the venous system at the junction of the left subclavian vein and the left internal jugular vein. A series of valves generally facilitate one-way flow of lymphatic fluid into the venous system and prevent reflux of whole blood into the thoracic duct. Although not well studied, disruption of one or more of these valves may have negative consequences. Therefore, it may be desirable to protect these valves and/or the lymphatic vessels themselves from damage.

Under normal circumstances, the lung lymphatics absorb excess interstitial fluid and prevent alveolar fluid accumulation. In pulmonary edema, the lymphatic system is overwhelmed or ineffective as vascular pressure prevents forward flow or alveolar migration increases with membrane permeability.

Accordingly, reducing downstream pressure and/or increasing outflow from the lymphatic system may have a positive effect on pulmonary edema and limit the fluid accumulation in the lung. Such an approach has not been viable clinically, as thoracic duct cannulation historically has required an open surgical approach and irreversible transection of the distal duct.

SUMMARY

The present invention is directed generally to systems and methods for performing medical procedures. More particularly, the present invention is direct to systems and methods for performing medical procedures that include accessing the lymphatic system of a patient, e.g., to remove, separate, and/or re-infuse lymphatic fluid, e.g., to facilitate lung or other organ transplantation.

The systems and methods described herein and in the applications incorporated by reference herein may facilitate accessing the lymphatic system, e.g., to cannulate, drain, and/or otherwise capture lymphatic fluid within the thoracic duct to facilitate transplanting a lung or other organ.

In accordance with an exemplary embodiment, a method is provided for harvesting an organ from a donor body that includes introducing a distal end of a tubular member into the donor body's vasculature, and introducing the distal end of the tubular member into the donor body's thoracic duct. Fluid may be removed from the thoracic duct through the tubular member to a location exterior to the donor body, and one or more organs may be removed from the donor body.

In one embodiment, fluid may be removed substantially continuously from the thoracic duct until the one or more organs are removed. In another embodiment, fluid removal may be selectively removed to reduce fluid accumulation in the one or more organs, e.g., to reduce edema within a lung being harvested.

In accordance with another embodiment, a method is provided for harvesting an organ from a donor body that includes introducing a distal end of a tubular member into the donor body's vasculature, and introducing the distal end of the tubular member into the donor body's thoracic duct. One or more fluid parameters of fluid within the thoracic duct may be monitored via the tubular member, and one or more organs may be removed from the donor body.

In accordance with still another embodiment, a method is provided for screening viability of a potential donor body that includes introducing a distal end of a tubular member into the donor body's vasculature, and introducing the distal end of the tubular member into the donor body's thoracic duct. Fluid may be removed from the donor body's thoracic duct via the tubular member, and analyzed to determine compatibility of one or more organs from the donor body with a potential recipient body. Optionally, a distal end of a second tubular member may be introduced into the potential recipient body's vasculature via a percutaneous access site; and into the potential recipient body's thoracic duct. Fluid may be removed from the potential recipient body's thoracic duct; and analyzed relative to the fluid removed from the potential donor body to determine compatibility of one or more organs from the potential donor body with the potential recipient body. Once compatibility is confirmed, the one or more organs may be removed from the donor body, and implanted in the potential recipient body.

In accordance with yet another embodiment, a method is provided for implanting an organ from a donor body in a recipient body that includes introducing a distal end of a tubular member into the recipient body's vasculature, and introducing the distal end of the tubular member into the recipient body's thoracic duct. The organ from the donor body may be implanted in the recipient body, and fluid from the recipient body's thoracic duct may be removed via the tubular member to a location exterior to the patient's body to remove one or more donor cells from the organ to reduce graft-versus-host-disease (GVHD) in the recipient body. Optionally, the one or more donor cells may be separated from the fluid removed from the thoracic duct, and one or more components of the removed fluid may be introduced back into the recipient body.

In accordance with another embodiment, a system is provided for harvesting an organ from a donor body that includes a tubular member comprising a proximal end, a distal end sized for introduction into the donor body into a thoracic duct, and a lumen extending between the proximal and distal ends for removing fluid from the thoracic duct; a separator for removing one or more donor cells from the fluid removed from the thoracic duct; and an infusion device for introducing one or more components of the removed fluid back into the donor body.

Other aspects and features of the need for and use of the present invention will become apparent from consideration of the following description taken in conjunction with the accompanying drawings.

BRIEF DESCRIPTION OF THE DRAWINGS

It will be appreciated that the exemplary apparatus shown in the drawings are not necessarily drawn to scale, with emphasis instead being placed on illustrating the various aspects and features of the illustrated embodiments. The drawings illustrate exemplary embodiments of the invention, in which:

FIGS. 3A-3C are schematic views showing alternative relaxed shapes for the distal portion of an apparatus, such as that shown in FIG. 1.

FIGS. 4A-4C are details of alternative embodiments of distal tips that may be provided on an apparatus, such as that shown in FIGS. 1-2B.

FIG. 4D is a detail of another alternative embodiment of a retractable/advanceable distal tip that may be provided on an apparatus, such as that shown in FIGS. 1-2B.

DETAILED DESCRIPTION OF THE EXEMPLARY EMBODIMENTS

Figure 1:
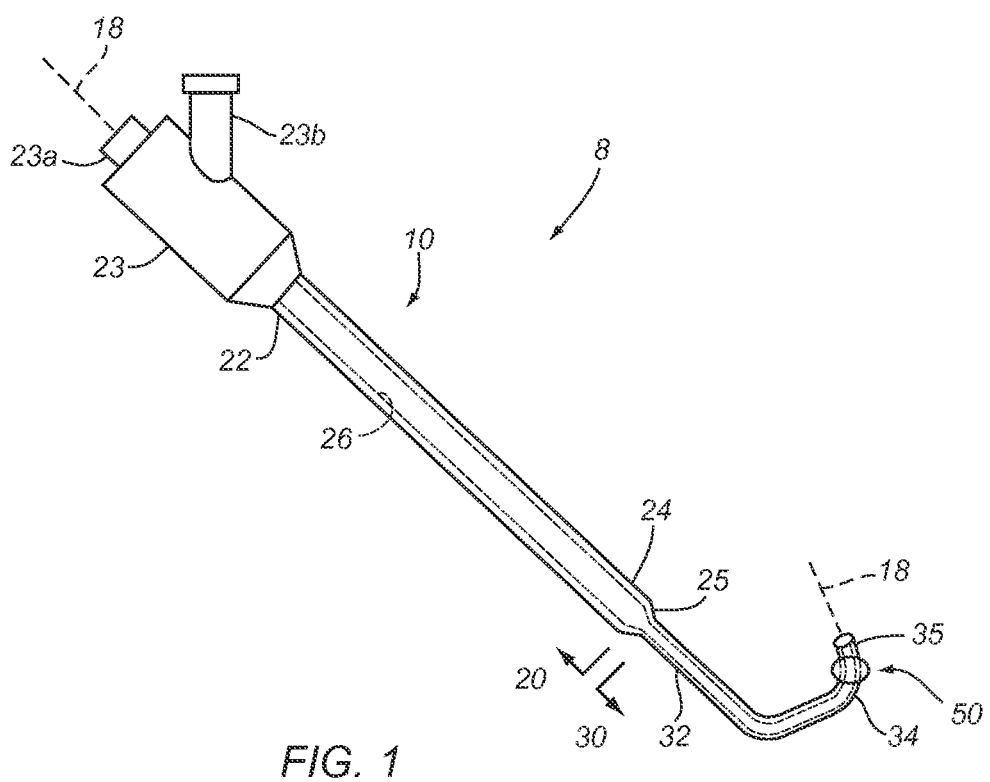
FIG. 1 is a perspective view of an exemplary embodiment of an apparatus for accessing a thoracic duct.
Figure 2A:
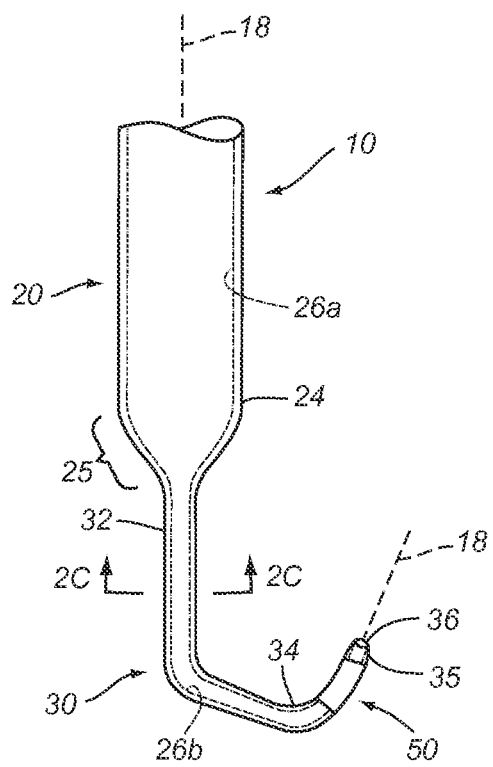
FIGS. 2A and 2B are details of a distal portion of the apparatus of FIG. 1, showing a balloon on the distal portion in collapsed and enlarged configurations, respectively.
Figure 2B:
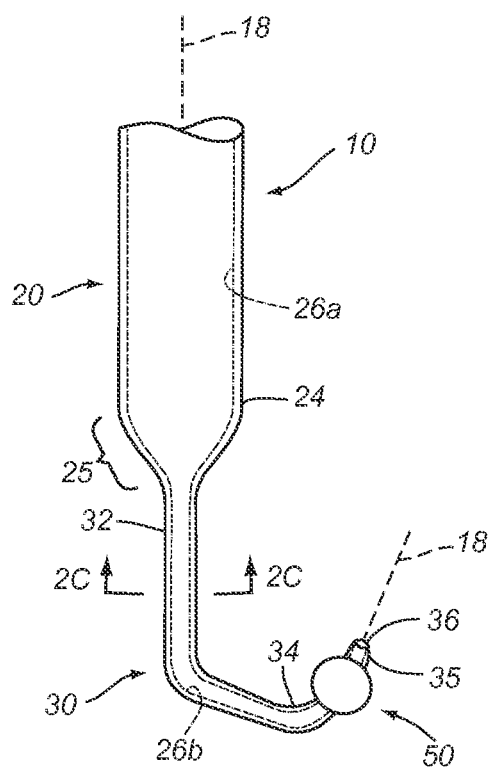

Turning to the drawings, FIGS. 1-2B show an exemplary embodiment of an apparatus 8 for accessing and/or isolating the lymphatic system of a patient 90 (not shown, see, e.g., FIG. 5 for anatomical references), e.g., to aspirate or otherwise draw lymphatic fluid from the thoracic duct 94, as described further below. Generally, the apparatus 8 includes a catheter or other tubular member 10 including a proximal or main portion 20, e.g., sized and/or shaped for introduction into a blood vessel of the patient, such as a jugular vein 92b (not shown, see FIG. 5), and a relatively smaller distal portion 30, e.g., sized and/or shaped for introduction into a thoracic duct 94 of the patient 90 (also not shown, see FIG. 5), thereby defining a central longitudinal axis 18 for the apparatus 8.

A balloon or other expandable member 50 may be provided on the distal portion 30, e.g., sized for introduction into a thoracic duct in a collapsed configuration and expandable to an enlarged configuration for substantially sealing and/or isolating the thoracic duct 94, as described further below. The balloon 50 may be formed from elastic material, e.g., such that the balloon 50 may be inflated to multiple diameters to accommodate engaging the wall of thoracic ducts of various sizes and/or shapes, to provide a substantially fluid-tight seal without applying excessive forces against the wall.

Figure 5:
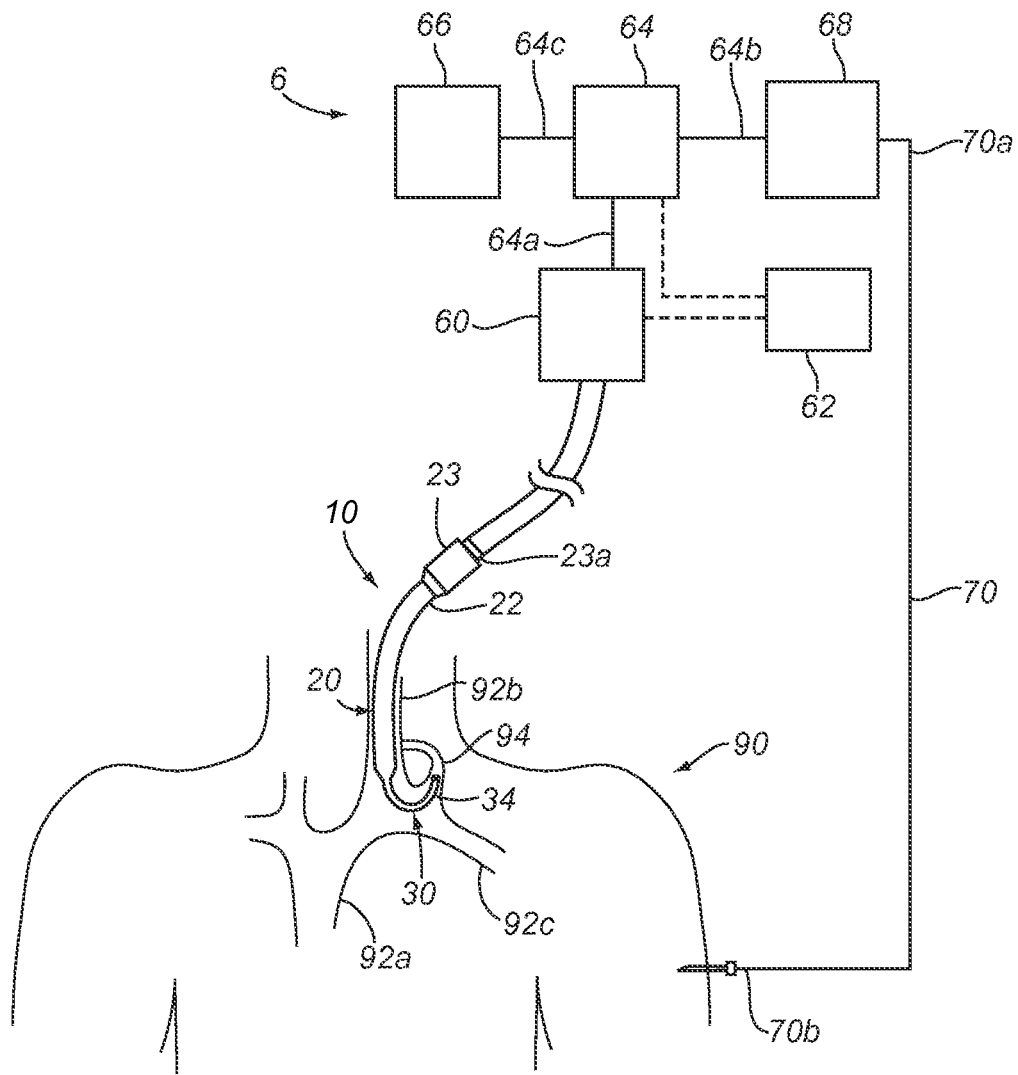
FIG. 5 is a detail of a patient's body showing a schematic of an exemplary system for accessing the lymphatic system of the patient including an apparatus, such as that shown in FIGS. 1-2B.

Generally, the proximal and distal portions 20, 30 of the catheter 10 have different dimensions and/or properties. For example, the proximal portion 20 may have a substantially straight shape in a relaxed state, yet may be sufficiently flexible to be introduced into a patient's body 90, e.g., sufficiently flexible to be introduced into the venous system from a percutaneous access site, such as via a left or right internal or external jugular vein, subclavian vein, axillary vein, or other percutaneous access site. In an exemplary embodiment, access may be gained from the left internal jugular vein 92b to approach the junction of the left internal jugular vein 92b and left subclavian vein 92c, as shown in FIG. 5. The distal portion 30 may have a curvilinear shape in a relaxed state, e.g., a simple curved shape or a more complicated shape including one or more curved and/or straight sections, which may facilitate introduction of the distal portion 30 into the thoracic duct 94, e.g., from the jugular vein 92b, as described further below.

In addition or alternatively, the proximal portion 20 may be substantially longer than the distal portion 30, e.g., to allow the proximal portion 20 to be introduced into the patient's body from an access site, e.g., into the left internal jugular vein 92b, and manipulated to introduce the distal portion 30 into the thoracic duct 94. For example, as shown in FIG. 1, the proximal portion 20 may include a proximal end 22 including a handle or hub 23, and a distal end 24 coupled or otherwise including a transition 25 to the distal portion 30. In exemplary embodiments, the proximal portion 20 may have a length from the handle 23 to the transition 25 between about three and one hundred twenty centimeters (3.0-120 cm), or alternatively between about three and thirty centimeters (3.0-30.0 cm), and may have an outer diameter or other maximum cross-section between about one and seven millimeters (1.0-7.0 mm), or alternatively between about one and three millimeters (1.0-3.0 mm). The handle 23 may be larger than the proximal portion 20, e.g., having a shape and/or otherwise configured for holding and/or manipulating the catheter 10 from a location outside of a patient's body.

The transition 25 may include a tapered shape, as shown, an abrupt step-down shape (not shown), and the like to transition between the proximal and distal portions 20, 30. If the proximal and distal portions 20, 30 are formed from different materials, the transition 25 may connect the different materials together, e.g., by bonding with adhesive, fusing, sonic welding, heat forming, and the like.

The distal portion 30 may have a proximal end 32 extending distally from the transition 25, e.g., aligned substantially axially with the proximal portion 20, and a distal end 34 terminating in a distal tip 35. In exemplary embodiments, the distal portion 30 may have a length from the proximal end 32 to the distal tip 35 between about one and twenty centimeters (1.0-20.0 cm) or between about one half and ten centimeters (0.5-10.0 cm), and may have an outer diameter or other maximum cross-section between about half to five millimeters (0.5-5.0 mm), or alternatively between about half and two millimeters (0.5-2.0 mm). Thus, the distal portion 30 may be substantially shorter than the proximal portion 20, e.g., such that the proximal portion 20 may extend from a percutaneous access site (not shown) into the junction of the left internal jugular vein 92b and the left subclavian vein 92c, and the distal portion 30 may simply curve and enter the thoracic duct 94, as described further elsewhere herein.

The distal portion 30 may have a substantially uniform outer diameter between the proximal end 32 and the distal tip 35, or the diameter may vary, e.g., tapering at or adjacent the distal tip 35 to provide a substantially atraumatic distal tip 35.

In addition, the distal portion 30 may have a flexibility greater than the proximal portion 20. For example, the proximal portion 20 may have sufficient column strength, stiffness, torque, and the like such that the proximal portion 20 may be manipulated from the handle 23 without substantial risk of the distal end 24 of the proximal portion 20 buckling or kinking, while providing sufficient flexibility to accommodate introduction into curved vessels within the patient's body. In exemplary embodiments, the proximal portion 20 may have a substantially rigid or semi-rigid proximal end 22, e.g., to facilitate advancement of the distal portion from the handle 23, while the distal end 24 may be semi-rigid or flexible. Moreover, the device properties may be optimized to responsively translate manipulation of the proximal end 22 into movement of the distal portion 30, e.g. by means of rotation, torque, angular manipulation, withdrawal, and/or advancement.

Optionally, the distal portion 30 may have sufficient length to extend only through one or more valves (not shown) at the outlet of the thoracic duct 94. Alternatively, the distal portion 30 may have a length to extend further into the thoracic duct 94, e.g., to a location adjacent desired organs within the patient's body, e.g., above the diaphragm and/or adjacent or into one or more target tributaries, such as the hylar lymphatic vessels or lymph nodes (not shown), as described elsewhere herein. In the latter embodiment, the distal portion 30 may have a desired rigidity to facilitate advancement into the desired location within the thoracic duct 30 and/or tributary. For example, if the apparatus 8 is intended for introduction into the thoracic duct 94 of an organ recipient or other patient, the distal portion 30 may be substantially flexible and/or atraumatic to minimize the risk of injury to the patient's thoracic duct or other anatomy. In contrast, for an organ donor, such as a lung donor, the distal portion 30 may be semi-rigid and/or otherwise configured to facilitate insertion and/or other manipulation where there is less concern for injury to the donor's anatomy.

In an exemplary embodiment, the distal portion 30 may be substantially flexible, e.g., biased to the curvilinear shape when free from external forces, yet flexible to accommodate bending, compressing (of the distal tip 35 towards the proximal portion 20), and/or other movement of the distal portion 30 to facilitate introducing the distal tip 35 into the thoracic duct. In exemplary embodiments, the distal portion 30 may be formed from PEBAX, urethane, silicone, and/or other soft and/or flexible materials, e.g., having substantially uniform properties along the length of the distal portion 30, or becoming progressively (or otherwise) softer and/or more flexible from the proximal end 32 to the distal tip 35. The proximal and distal portions 20, 30 may be formed from different materials to provide the desired flexibility. For example, the proximal portion 20 may include a reinforcement layer, e.g., braiding and the like between inner and outer layers (not shown), while the distal portion 30 may simply include a single layer or vice versa. Alternatively, a different reinforcing layer (e.g. braid, coil, stent-like structure or other scaffolding) may be used in the proximal and distal portions 20, 30. For example, a reinforcing structure may include a laser-cut tubular structure (e.g., formed from Nitinol, stainless steel, cobalt chromium, and the like) having a structure that may accommodate a substantially straight shape and a desired curvilinear shape without substantial permanent deformation. Further, a reinforcing structure may be shape set (e.g., by heat treating, annealing, plastically deforming, and the like) in order to maintain a desired curvilinear shape in the distal portion 30.

In addition or alternatively, relative flexibility may be obtained by providing different wall thicknesses, e.g., from the same or different materials. For example, as shown in FIGS. 2A and 2B, the proximal portion 20 may have a relatively larger wall thickness than the distal portion 30, which may enhance relative flexibility of the distal portion 30. In exemplary embodiments, the wall thickness of the proximal portion 20 may be between about 0.1 and three millimeters (0.1-3.0 mm), while the wall thickness of the distal portion 30 may be between about 0.1 and two millimeters (0.1-2.0 mm).

As shown in FIG. 1, the distal portion 30 may include multiple substantially straight sections between curved sections, e.g., to provide a "hook" shape having an overall angle of curvature equal to or greater than ninety degrees, e.g., between about ninety and three hundred sixty degrees)(90-360°, or between about ninety and one hundred fifty degrees)(90-150°. Such radii of curvature may facilitate introduction into the thoracic duct 94, which may connect near the junction of the jugular, subclavian, and brachiocephalic veins 92 at an acute angle, such that a radius of curvature greater than ninety degrees)(90° may be necessary to align the distal tip 35 with the thoracic duct 94 when the proximal portion 20 is within the left internal jugular vein 92b, as described further elsewhere herein.

In an alternative embodiment, shown in FIG. 3A, the distal portion 30a may include a single substantially continuous radius of curvature approaching one hundred eighty degrees (180°). In a further alternative, shown in FIG. 3B, the distal portion 30b may have a more complicated curvilinear shape, e.g., including a first straight section between a bend and a radiused section ending in a substantially straight distal tip (which may carry a balloon, not shown). In yet another alternative, shown in FIG. 3C, the distal portion 30c may include a continuous curved shape including a first bend in an opposite direction to the main radius of curvature of the distal portion 30c. Such shapes may orient the distal tip 35 of the catheter 10 back towards the proximal end 22 with the distal tip 35 defining a desired angle relative to the longitudinal axis 18 within the proximal portion 20.

In still another alternative, the distal portion 30 may include a curved section of constant or variable radius having an arc angle of between about zero and three hundred sixty degrees (0°-360°) and a radius of curvature between about one and fifteen millimeters (1.0-15.0 mm). Further alternatively, the distal portion 30 may include one or more discrete bends, creating a distal shape having a width between about two and thirty millimeters (2.0-30.0 mm). More generally, any of the foregoing shapes may be optimized to locate the distal tip 35 at or near the thoracic duct ostium and simultaneously align the tip vector with the entry vector of the thoracic duct 94. Furthermore, the shape of the distal portion 30 may be sufficiently resilient to return to its pre-set shape, e.g. after introduction through a sheath, repeated manipulation, and the like.

Optionally, the distal portion 30 may include one or more features to facilitate identification and/or localization of the distal portion 30, e.g., the balloon 50 and/or distal tip 35, within a patient's body using external imaging. For example, one or more echogenic features, may be provided on or in the wall of the balloon 50 and/or on the distal tip 35, which may facilitate monitoring the distal portion 30 using ultrasound imaging. Such exemplary features may include doping or coating with tungsten, tungsten carbide, titanium dioxide, iron oxide, zinc oxide, platinum, gold, barium, bismuth, and/or titanium; echogenic surface modifications such as reflective gratings, surface depression and/or projections; inclusions, for example, of glass particles, air bubbles, and the like, including those described in U.S. Pat. No. 5,921,933, the entire disclosure of which is expressly incorporated by reference herein. Alternatively, radiopaque and/or other markers (also not shown) may be provided to facilitate monitoring the distal portion 30 using fluoroscopy or other external imaging.

Returning to FIGS. 1-2B, the catheter 10 may include one or more lumens 26, 27 extending therethrough, e.g., from the proximal end 22 of the proximal portion 20 to the distal portion 30. For example, as shown in FIG. 1, an aspiration or infusion lumen 26 may be provided that communicates with a port 23a in the handle 23 and extends through the entire proximal and distal portions 20, 30 to one or more inlet (or outlet) ports 36 adjacent the distal tip 35. As best seen in FIGS. 2A and 2B, the aspiration lumen 26 may include a relatively large region 26a within the proximal portion 20 and a relatively small region 26b within the distal portion 30. In exemplary embodiments, the proximal region 26a of the lumen 26 may have an inner diameter (or other maximum cross-section) between about one and five millimeters (1.0-5.0 mm), while the distal region 26b may have an inner diameter (or other maximum cross-section) between about 0.1 and three millimeters (0.1-3.0 mm).

The smaller diameter of the distal region 26b may allow the outer diameter of the distal portion 30 to be minimized, e.g., to provide desired flexibility and/or minimize the size of the distal portion 30 to facilitate introduction into the thoracic duct 94, while the larger diameter of the proximal region 26a may allow lymph or other fluids to be drawn through the catheter 10 more easily. For example, the larger diameter over most of the length of the catheter 10 may expose the fluid to lower friction, which may increase flow rate and/or reduce the risk of lysing or otherwise damaging cells or other components of the fluid being aspirated or delivered through the lumen 26 of the catheter 10.

As shown in FIGS. 2A, 2B, and 4A, the aspiration lumen 26 may communicate with a single inlet port 36 in the distal tip 35, e.g., aligned with the central longitudinal axis 18. Alternatively, multiple inlet ports may be provided on the distal tip, e.g., to reduce the risk of a single or multiple ports becoming occluded with fluid or debris and/or contacting and sucking the wall of the thoracic duct or other body lumen against the distal tip 35, which may otherwise prevent fluid from being drawn into the lumen 26. For example, as shown in FIG. 4B, the distal tip 35a may include a plurality of side ports in addition to the axial inlet port 36a, or, as shown in FIG. 4C, one or more slots (two shown) may be provided that extend partially from the axial inlet port 36b.

Figure 2C:
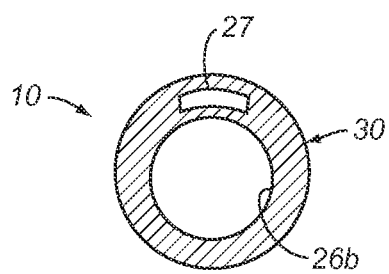
FIG. 2C is a cross-section of the distal portion of the apparatus of FIGS. 2A-2B taken along line 2C-2C.

In addition, turning to FIG. 2C, the catheter 10 may include an inflation lumen 27, e.g., extending through the proximal and distal portions 20, 30 and communicating with an interior of the balloon 50. The inflation lumen 27 may communicate with a port 23b on the handle 23, shown in FIG. 1, which may allow a source of inflation and/or vacuum, e.g., a syringe and the like (not shown), to be coupled to the catheter 10 and communicate with the interior of the balloon 50, e.g. to allow the balloon 50 to be inflated and collapsed, as described elsewhere herein. Alternatively, another expanded member, e.g., a mechanically expandable frame and the like (not shown, see, e.g., FIGS. 9A-9C), may be provided on the distal portion 30 instead of the balloon 30. In this alternative, a mechanical actuator, e.g., a slider, wheel, and the like (also not shown, may be provided on the handle 23 that is coupled to the frame or other expandable member for directing the expandable member between collapsed and enlarged configurations.

Optionally, the catheter 10 may include one or more additional lumens, if desired. For example, an infusion lumen (not shown) separate from the aspiration lumen 26 may be provided, which may allow infusion of fluids or agents through the catheter 10 to one or more outlets (also not shown) on the distal portion 30, independent of aspiration or removal of fluid through the lumen 26. Infusion of fluids may be into the thoracic duct 94 or into the vein(s) at any point along the course of the catheter 10. Infused fluids may include at least some part or all of fluids aspirated by means of the same catheter. In addition, a guidewire lumen and/or a stylet lumen (not shown) may be provided that extends through the proximal portion 20 into the distal portion 30, e.g., for at least partially straightening and/or supporting the distal portion 30 during introduction into a patient's body, as described elsewhere herein.

Figure 6:
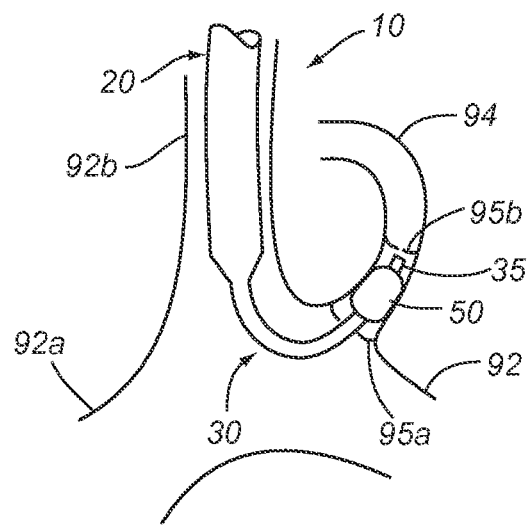
FIG. 6 is a detail of a patient's body, showing the distal portion of a catheter positioned within a thoracic duct of the patient and with a balloon thereon inflated to substantially isolate the thoracic duct from the patients venous system.

Turning to FIGS. 5 and 6, the apparatus 8 (or any other embodiment described herein or in the applications incorporated by reference herein) may be used to perform a medical procedure within the patient's body 90 that includes accessing the thoracic duct 94, which may be related to any of the conditions and/or treatments described elsewhere herein. For example, an apparatus 8 may be introduced into a donor's body during an explantation procedure in which one or more organs are removed for implantation in a recipient or other patient's body. In addition or alternatively, an apparatus 8 may be introduced into a recipient's body during an implantation procedure, as described elsewhere herein.

Initially, the catheter 10 may be introduced into the patient's body 90, e.g., into the venous system from a percutaneous access site, such as the left or right internal or external jugular, subclavian, axillary, anterior cubital, or femoral veins. To facilitate introduction and/or navigation of the catheter 10, one or more other devices may be used in conjunction with the catheter 10, if desired.

For example, in one embodiment, a guidewire (not shown) may be introduced and advanced from the percutaneous access site, through any intervening vessels into the junction of the left internal jugular vein 92b and left subclavian vein 92c, and into the thoracic duct 94. The guidewire may be backloaded into the inlet port 36 of the distal portion 30 and through the aspiration lumen 26 (or through a separate lumen, e.g., a dedicated guidewire lumen, not shown, if provided on the catheter 10). The catheter 10 may then be advanced over the guidewire into the access site and intervening vessels, and at least the distal tip 35 of the distal portion 30 may be introduced into the thoracic duct 94.

In addition or alternatively, other devices may be used to at least partially straighten and/or otherwise support the distal portion 30 of the catheter 10. For example, a stylet (not shown) may be positioned within the catheter 10, e.g., within the aspiration lumen 26 or a separate lumen (not shown) such that the stylet enters at least partially into the distal portion 30, thereby directing the distal portion 30 from its relaxed curvilinear shape to a less curved or substantially straight configuration (not shown) and/or otherwise supporting the distal portion 30 from buckling or kinking. The distal portion 30 may then be introduced through the access site and any intervening vessels until the distal tip 35 is located adjacent the thoracic duct 94, e.g., within the junction of the jugular and subclavian veins 92b, 92c. The stylet may be sufficiently flexible to accommodate introducing the distal portion 30 through any bends or tortuous anatomy encountered between the access site and the thoracic duct 94. Once the distal tip 35 is located adjacent the thoracic duct 94, e.g., within the junction of the left internal jugular vein 92b and the left subclavian vein 92b, the stylet may be removed, thereby allowing the distal portion 30 to return towards its relaxed, curvilinear configuration. Alternatively, one or more shaped stylets may be used to accentuate, alter, and/or essentially create the shape of the distal portion 30. Further, a stylet may be used to direct the distal portion 30 toward and/or into the thoracic duct 94, e.g., by independent and/or co-manipulation (e.g. twisting, advancing, retracting) of the stylet and the catheter 10.

In another alternative, a sleeve, sheath, cover, and the like (also not shown) may be provided over the catheter 10 until the distal portion 30 is sufficiently covered, e.g., to at least partially straighten and/or support the distal portion 30. The distal portion 30 may then introduced into the patient's body 90 until the distal tip 35 is disposed adjacent the thoracic duct 94, whereupon the cover may be removed to expose and release the distal portion 30, again thereby allowing the distal portion 30 to return towards its relaxed, curvilinear configuration.

With the distal portion 30 released or exposed within the junction, the proximal portion 20 of the catheter 10 may then be manipulated, e.g., advanced and/or retracted, rotated, and the like until the distal tip 35 enters the thoracic duct 94, as shown in FIG. 5. For example, without a guidewire, the catheter 10 may be manipulated until the distal portion 30 "hooks" the ostium of the thoracic duct 94. Because of the soft and/or flexible nature of the distal portion 30, such manipulation may be completed without substantial risk of perforation or other damage to the vessels. In addition, given that the thoracic duct 94 may extend at an angle almost one hundred eighty degrees relative to the left internal jugular vein 92b, the angle of the distal portion 30 may facilitate orienting the distal tip 35 "backwards" towards the ostium of the thoracic duct 94.

Once the distal tip 35 is placed within the ostium of the thoracic duct 94, the catheter 10 may be retracted or otherwise manipulated to direct the distal portion 30 further into the thoracic duct 94. For example, if the catheter 10 is to be introduced into the left internal jugular vein 92b, as shown in FIG. 5, the length of the catheter 10 may be substantially shorter than most catheters, thereby providing a more direct relationship of movement between the proximal end 22 and the distal portion 30 since the catheter 10 is less likely to twist, compress, stretch, and the like between the proximal end 22 and the distal portion 30.

If the catheter 10 is manipulated to place the distal tip 35 at the ostium of the thoracic duct 94, the catheter 10 may simply be retracted (e.g., upwardly) to pull the distal tip 35 up into the thoracic duct 94, e.g., as shown in FIG. 6. In an exemplary embodiment, the distal portion 30 may pass through the terminal valve 95a of the thoracic duct 94 until the balloon 50 is positioned between the terminal valve 95a and the next valve 95b within the thoracic duct 94. The balloon 50 may then be inflated to engage the wall of the thoracic duct 94 and substantially seal and/or isolate the thoracic duct 94 from the veins 92.

Optionally, navigation to the thoracic duct 94 may be aided using external imaging, such as ultrasound imaging. For example, as described elsewhere herein, the distal portion 30 of the catheter 10 may include one or more echogenic features, which may facilitate identification and monitoring the balloon 50 and/or the distal tip 35. Because the thoracic duct 94 is located near the surface, i.e., close to the patient's skin, an ultrasound imaging device placed on or near the patient's skin may provide high resolution visualization of the region including the thoracic duct 94 and adjacent veins 92 to facilitate monitoring the distal portion 30 until the distal tip 35 and balloon 50 are positioned as desired.

In addition or alternatively, tactile feedback and/or manipulation may be used to facilitate positioning the distal portion 30. For example, given the close proximity of the thoracic duct 94 and neighboring veins 92 to the skin, it may be possible to feel the catheter 10 by placing the user's fingers on the patient's overlying skin and pressing against the skin and intervening tissues. Such pressure may also be used to physically manipulate the distal portion 30, e.g., in addition to manipulation of the proximal end 22, to direct the distal tip 35 into the thoracic duct 94.

In addition or alternatively, other imaging may be used, such as fluoroscopy, MRI, CT, and/or direct visualization, e.g., using an imaging element carried on the distal portion 30 of the catheter 10. Exemplary imaging elements and methods for using them are disclosed in U.S. Publication Nos. 2011/0034790, 2007/0015964, 2006/0084839, and 2004/0097788, the entire disclosures of which are expressly incorporated by reference herein.

Optionally, with further reference to FIG. 6, additional methods may be used to facilitate introducing the distal tip 35 and balloon 50 through the terminal valve 95a, e.g., instead of simply pushing the distal tip 35 through the valve 95a. For example, the terminal valve 95a may be monitored using external imaging or otherwise monitored to coordinate timing of movement of the terminal valve 95a with physiological events, e.g., heart rate, and the like, until the terminal valve 95a naturally opens, whereupon the distal tip 35 may be advanced through the open valve 95a into the thoracic duct 94. Alternatively, the user may trigger opening of the terminal valve 95a, e.g., by increasing lymph within the patient's body, for example, by squeezing tissue in the arm or leg.

In another alternative, a negative pressure may be created within the junction, e.g., by aspirating into the catheter 10 or otherwise, with the resulting vacuum causing the terminal valve 95a to open and allow the distal tip 35 to be advanced into the thoracic duct 94. In other alternatives, the user may simply periodically probe the terminal valve 95a by gently advancing the distal tip 35 against the valve 95a and/or by rotating the catheter 10 to screw the distal tip 35 through the valve 95a. Further alternatively, the balloon 50 (or other distal expandable member) may be at least partially expanded to assist in centering the distal tip 35 in or near the ostium in order to more easily cross the valve 95a.

In yet another alternative, a helical tip member (not shown) may be provided on the distal portion 30 that extends from the distal tip 35, which may be rotated to guide the distal tip 35 through the terminal valve 95a. In these alternatives, the distal portion 30 may pass through the terminal valve 95a until the balloon 50 is positioned between the terminal valve 95a and the next valve 95b within the thoracic duct 94. The balloon 50 may then be inflated to engage the wall of the thoracic duct 94 and substantially seal and/or isolate the thoracic duct 94 from the veins 92.

With the balloon 50 expanded to substantially isolate the thoracic duct 94, fluid may be aspirated into the lumen 26 of the catheter 10 and collected, e.g., as described elsewhere herein, fluid may be delivered into the thoracic duct 94, and/or other desired procedures may be performed via the thoracic duct 94.

In an alternative embodiment, shown in FIG. 4D, the catheter 10' may include a movable distal tip 35,' which may be directed axially closer to or away from the balloon 50.' For example, the balloon 50' may be attached to the distal end of an outer tubular member 30,' and an inner tubular member 37' may extend through the outer tubular member 30' and the balloon 50,' and terminate in the distal tip 35.' Thus, movement of the inner tubular member 37' relative to the outer tubular member 30' may move the distal tip 35' relative to the balloon 50.' In this alternative, the balloon 50' may serve to substantially center the distal tip 35' relative to the valve(s) 95 within the thoracic duct 94 (not shown in FIG. 4D), e.g., such that the distal tip 35' may be advanced or retracted as desired relative to the valve(s) 95 to facilitate access, removal of fluid, and/or performing other procedures within the thoracic duct 94.

Optionally, the suction pressure used to aspirate lymph within the thoracic duct 94 may be adjusted, e.g., to substantially match the individual patient's maximum lymph flow. If the patient lymph flow changes over time, this method anticipates adjustment of pressure over time, both decreasing suction pressure over time, and increasing suction pressure over time, as desired.

In another option, fluids or other substances may be infused into the thoracic duct 94 or vein via the catheter 10, if desired, e.g., in a substantially continuous or oscillatory manner. For example, one or more of the following may be infused: blood contaminated lymph, lymph with greater concentrations of desired substances, and the like, as described elsewhere herein.

In another embodiment (not shown), the catheter may include a distal end and a balloon sized to be introduced further into the thoracic duct. For example, the distal end may be advanced beyond a valve in the thoracic duct such that the balloon may be inflated beyond the valve. In addition or alternatively, the catheter may include one or more other features for securing and/or sealing distal to a valve, including one or more compliant rings, radial filaments/brushes, and/or other passive fixation devices (not shown) that may at least partially resist retraction or avoid spontaneous dislodgement of the catheter during use. In addition or alternatively, active fixation, such as suction, may be used to substantially fix the distal end of the catheter at a desired location, e.g., within the thoracic duct.

Figure 7A:
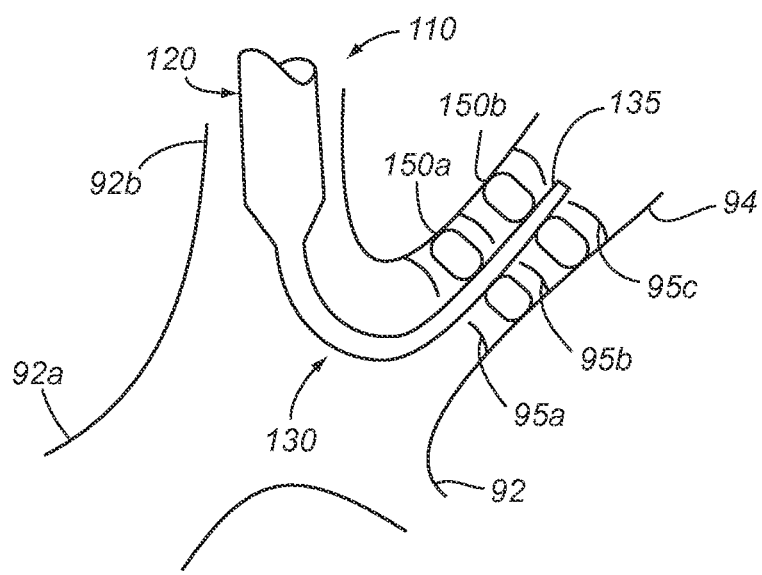
FIGS. 7A and 7B are details of a patient's body, showing a distal portion of another exemplary embodiment of an apparatus with a pair of balloons expanded within a thoracic duct of the patient on either side of a valve within the thoracic duct.
Figure 7B:
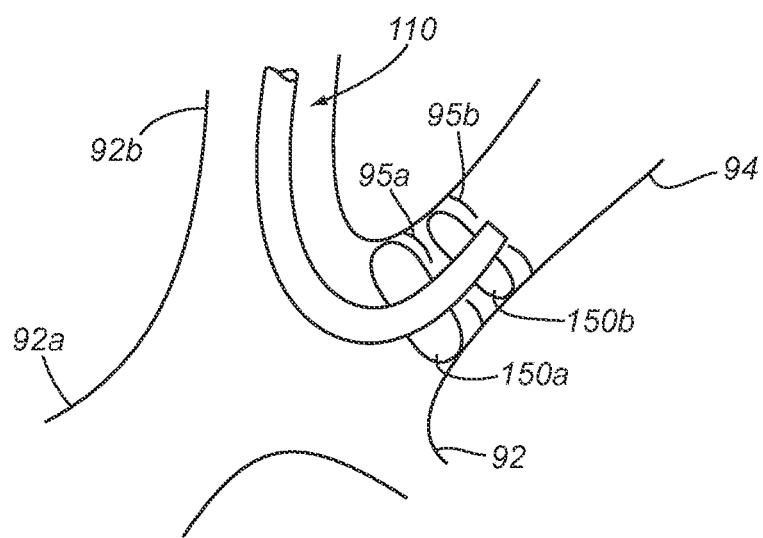

Turning to FIGS. 7A and 7B, another embodiment of a catheter 110 is shown that includes a pair of balloons 150 spaced apart axially from one another on a distal portion 130 of the catheter 130. The balloons 150 may communicate with a single inflation lumen (not shown) such that the balloons 150 may be inflated and/or collapsed substantially simultaneously. Alternatively, the balloons 150 may communicate with separate inflation lumens (also not shown) such that the balloons 150 may be inflated and/or collapsed independently of one another. The catheter 110 may have a size, length, and/or shape configured to be introduced and/or manipulated using a handle or hub on a proximal end (not shown) of the catheter 110, similar to other embodiments herein.

As shown in FIGS. 7A and 7B, a distal tip 135 of the catheter 110 may be introduced into the thoracic duct 94 until the balloons 150 pass beyond the terminal valve 95a. Optionally, as shown in FIG. 7A, the balloons 150 may be spaced apart sufficiently from one another such that the balloons may be provided on either side of the next valve 95b within the thoracic duct 94, i.e., with a proximal balloon 150a between a first and second valve 95a, 95b, and a distal balloon 150b between the second and third valves 95b, 95c. Such an arrangement of balloons 150 may provide enhanced stability for the distal portion 130 and/or improved sealing of the thoracic duct 94.

Optionally, the balloons 150 may be configured such that the balloons 150 may be positioned with a valve 95b located between the balloons 150. When the balloons 150 are inflated, they may squeeze or otherwise engage the valve 95b to enhance sealing of the thoracic duct 94 using the valve 95b in addition to the balloons 150 engaging the wall of the thoracic duct 94. In another option, shown in FIG. 7B, the balloons 150 may be positioned on either side of the terminal valve 95a such that the distal balloon 150b is positioned between the first and second valves 95a, 95b, and the proximal balloon 150a engages the ostium of the thoracic duct 94 outside the terminal valve 95a, which may reduce the risk of blood entering the thoracic duct 94 from the veins 92. Further alternatively, the balloons 150 may be slidably disposed relative to one another (not shown) such that they may be brought together or moved apart, e.g., to capture and/or release a valve positioned between them. Further alternatively, one or more balloons may include different surface properties, e.g. a lubricious distal surface (e.g., using a hydrophilic coating, lubrication, surface features, and the like), e.g., to facilitate valve crossing and a less lubricious proximal surface to, e.g. to decrease the chance of inadvertent removal.

Figure 8:
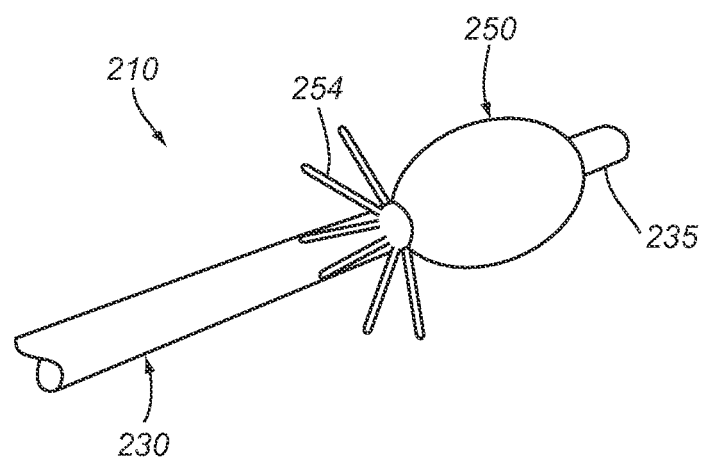
FIG. 8 is a detail showing a distal portion of another embodiment of a catheter including a plurality of expandable tines adjacent a balloon for anchoring the distal portion relative to a thoracic duct.

Turning to FIG. 8, still another embodiment of a catheter 210 is shown that includes a plurality of tines 254 on the distal portion 230 adjacent the balloon 250. The tines 254 may be biased to expand outwardly, but may be compressible inwardly, e.g., using an external sleeve or other constraint (not shown), which may be removed, e.g., after positioning the balloon 250 at a desired position within a thoracic duct (also not shown). When the tines 254 are deployed, they may engage the wall of the thoracic duct to anchor the distal portion 230 to prevent movement even if the balloon 250 is collapsed. The tines 254 may include substantially blunt free ends to engage the thoracic duct without penetrating or damaging the wall, or may include sharpened tips and/or barbs (not shown), which may be substantially permanently or indefinitely engage the wall of the thoracic duct. Thus, this embodiment may be used to secure the catheter 210 substantially indefinitely, e.g., for a long-term implant that is used to intermittently isolate the thoracic duct by expanding the balloon 250, e.g., to collect lymph. When not needed, the balloon 250 may be collapsed allowing normal function of the thoracic duct while the tines 254 prevent migration of the catheter 210 from the thoracic duct. If desired, the catheter 210 may be removed, e.g., by directing a sheath or other tubular member (not shown) into the thoracic duct to recapture and/or otherwise collapse the tines 254.

Alternatively, other features may be provided on the catheter, e.g., in addition to or instead of the tines 254 to maintain the distal end of the catheter 210 (or any of the embodiments herein) in a desired position, e.g., within the thoracic duct. Exemplary features may include providing silicone or other anti-slip materials on the distal end, a Nitinol or other expandable anchoring structure, an anchor ring, and the like (not shown).

Figure 9A:
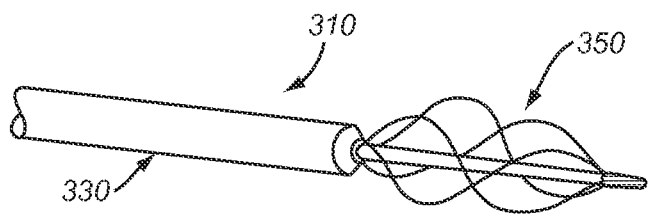
FIGS. 9A-9C are side and ends views of yet another embodiment of a catheter including a mechanically expandable member that is expandable from a collapsed configuration (FIG. 9A) to an enlarged configuration (FIGS. 9B and 9C) for isolating a thoracic duct.
Figure 9B:
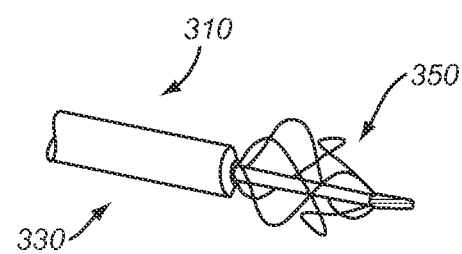
Figure 9C:
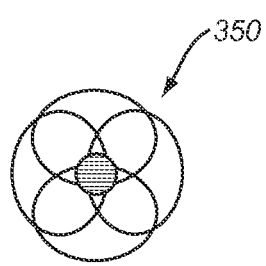

Turning to FIGS. 9A-9C, another embodiment of a catheter 310 is shown that includes an expandable frame 350 on a distal portion 330 including a set of wires or struts that may be manipulated from a proximal end (not shown) of the catheter 310. For example, an actuator on the proximal end (not shown) may be activated to direct the frame from a collapsed configuration (shown in FIG. 9A) to an enlarged configuration (shown in FIG. 9B). The size of the frame 350 may be sufficient to engage a wall of a thoracic duct when the distal portion 330 is introduced into the thoracic duct, as described elsewhere herein.

As shown in FIG. 9C, the frame 350 may carry a nonporous membrane that may be directed across the thoracic duct when the frame 350 is expanded to substantially seal the thoracic duct. Thus, the frame 350 may operate similar to the balloons described elsewhere herein, except that the frame 350 is mechanically actuated rather using fluid to inflate and collapse the balloons.

Figure 10:
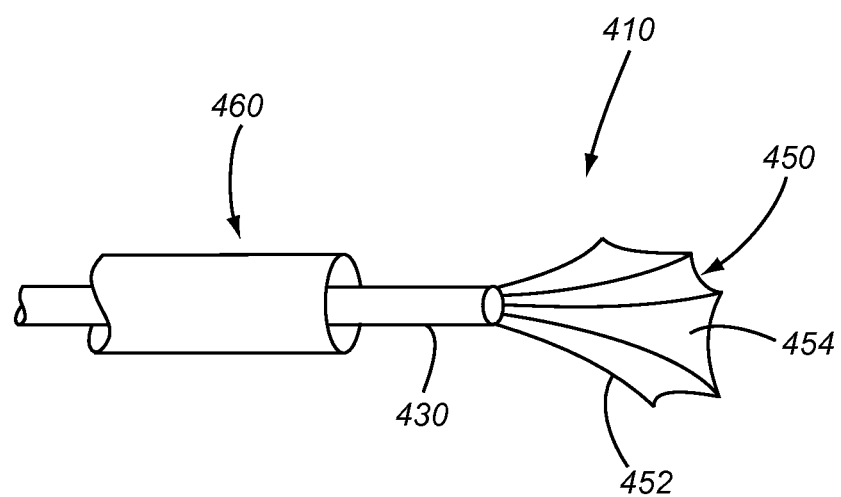
FIG. 10 is a side view of still another embodiment of a catheter including an expandable umbrella/hood shown in an expanded configuration upon deployment from a delivery sheath.

Turning to FIG. 10, yet another embodiment of a catheter 410 is shown that includes an expandable frame 450 on a distal portion 430 including a set of wires or struts 452 carrying a non-porous membrane 454. The frame 450 may be biased to an enlarged configuration, e.g., in which the struts are shaped to engage and/or enter the ostium of a thoracic duct, yet may be resiliently compressed into a delivery configuration, e.g., when placed within a delivery catheter 460. Alternatively, the frame 450 may be actuated from a proximal end (not shown) of the catheter 410, e.g., similar to the previous embodiments. The size of the frame 450 may be sufficient to engage the ostium adjacent the thoracic duct, or may be sized for introduction into the thoracic duct such that the membrane 454 sealingly engages the wall of the thoracic duct, e.g., when the distal portion 430 is introduced into the thoracic duct on either side of one or more valves, similar to other embodiments herein.

In another alternative embodiment, an expandable member (such as the balloon(s) 50, 150 or the frame 450) may be provided on a distal portion of a catheter distally beyond an inlet port communicating with the catheter's aspiration lumen (not shown). In this alternative, the expandable member may be used to substantially isolate a distal portion of the thoracic duct, i.e., distally beyond the expandable member from a proximal portion of the thoracic duct, i.e., proximal to the expandable member, thereby allowing fluid to be removed from and/or delivered into the proximal portion of the thoracic duct.

Turning to FIG. 5, the apparatus 8 shown in FIG. 1 (or any of the other embodiments described herein or in the applications incorporated by reference), may be part of a system 6 including one or more external components for performing a medical procedure, e.g., which may involve removing lymphatic fluid from the patient's body 90 via the thoracic duct 94, introducing agents or devices (not shown) into the thoracic duct 94, and/or infusing the removed lymphatic fluid, components thereof, and/or other agents into other locations within the patient's body 90. For example, one or more external devices may be provided that are coupled to the proximal end 22 of the catheter 10, e.g., for detecting, separating, collecting, and/or infusing lymphatic fluid and/or other fluids, as described in U.S. Publication No. 2011/0276023, the entire disclosure of which is expressly incorporated by reference herein. The external components may be provided integrated into a single device or may be provided as separate discrete components that are coupled to one another (e.g., along a fluid path, electrically, and/or otherwise).

In the example shown schematically in FIG. 5, the external components may include a detector or analyzer 60, a controller 62, a separator or filter 64, a waste container 66, a storage container 68, and an infusion device 70. One or more of the components may include a pump or source of vacuum or pressure, e.g., for removing fluid from the patient's body and/or delivering fluid into the patient's body 90 via the catheter 10, or infusing fluids via the infusion device 70, as described further below. In alternative embodiments, one or more of the components may be omitted. For example, the catheter 10 may simply be coupled directly to the storage container 68, e.g., with or without a source of vacuum to facilitate collection of lymphatic fluid (and any agents that end up within the lymphatic system).

The detector 60 may be coupled to the proximal end 22 of the catheter 10, e.g., to the port 23a on the handle 23, for receiving fluids that are drawn through the lumen 26 of the catheter 10 from the inlet port 36 in the distal tip 35 (not shown in FIG. 5, see, e.g., FIGS. 2A, 2B). The detector 60 may include one or more sensors (not shown), e.g., for distinguishing between lymphatic fluid and blood. In addition or alternatively, one or more sensors may be provided on the distal end 34 of the catheter 10, e.g., to detect when the thoracic duct is accessed and/or sealed from the venous system. In exemplary embodiments, the sensor(s) may include one or more optical sensors (e.g., for detecting the presence of red blood cells by light transmission or reflection characteristics), chemical sensors (e.g., for detecting one or more of pH, oxygen concentration, lactate, leukocyte esterase, and the like), sensors for measuring hematocrit, electrical sensors (e.g., for measuring impedance), temperature sensors, mechanical sensors (e.g., for detecting pressure waves, which may differ between the venous system and the thoracic duct; for flow detection, e.g., by Doppler ultrasound), filter devices sized to constituents of whole blood, and the like. In addition or alternatively, a sensor may be provided that is adapted to detect the presence of an exogenous marker introduced into the lymphatic system, such as a dye (e.g., methylene blue), an ingested marker, a fluorescent marker, and the like.

For example, a pump or other source of vacuum or pressure (not shown) within or coupled to the detector 60 may be selectively activated, e.g., by the controller 62 (or alternatively manually by a user, if desired), to remove fluid from the patient's body via the catheter 10 through the detector 60 to the separator 64. The controller 62 may automatically analyze sensor data from the sensors to identify whether the fluid is lymphatic fluid, blood, or other fluid.

For example, if the controller 62 determines that the fluid includes blood, the controller 62 may direct the fluid to the waste container 66, e.g., through the separator 64 or directly. In addition or alternatively, if the controller 62 detects the presence of a significant amount blood in the fluid (based on data from the detector 60 or otherwise) or detects a loss of seal (e.g., due a sudden pressure change in the fluid being removed via the catheter 10), the controller 62 may shut down the pump, close a shut-off valve (not shown) in the detector 60, or otherwise stop flow of fluid from the catheter 10 into the detector 60 and/or the rest of the system 6. This safety mechanism may be active, i.e., shut down automatically, or passive, i.e., merely warn the user.

In an exemplary embodiment, the separator 64 may include a valve (not shown) including an inlet 64a that communicates with the detector 60, a first outlet 64b communicating with the storage container 68, and a second outlet 64c communicating with the waste container 66. The valve may be selectively operable between the first and second outlets 64b, 64c by the controller 62, e.g., to direct undesired fluid, e.g., blood, to the waste container 66, and desired fluid, e.g., lymphatic fluid or components thereof, to the storage container 68. Alternatively, or in addition, the separator 64 may include one or more devices for separating and/or filtering various components of lymphatic fluid, including various types of cells, proteins, electrolytes, water, and/or other constituent parts of lymphatic fluid, and/or target agents that have transited into the lymphatic system. For example, chemotherapy or other agents may be substantially separated from other components in order to selectively remove the agents from a patient's body, e.g., to avoid systemic delivery of the agents, as described elsewhere herein.

If the controller 62 confirms that the fluid is lymphatic fluid, the controller 62 may activate the separator 64 to direct the lymphatic fluid or components of the lymphatic fluid into the storage container 68. For example, if the entire lymphatic fluid is to be collected, the separator 64 may simply divert the fluid into the storage container 68. Alternatively, it may be desirable to separate certain constituents of the removed fluid, e.g., lymphatic fluid, particular cells, proteins, and the like, and/or agents previously introduced into the patient's body. For example, the separator 64 may include one or more of a mechanical filtration system, an osmotic gradient system, a concentration gradient system, a centrifuge, and the like to separate the desired components from the rest of the fluid. Once separated, the desired components may be delivered to the storage container 68, while the rest of the fluid is delivered to the waste container 66.

Optionally, the controller 62 or other components of the system 6 may monitor the flow to keep track of the amount of fluid extracted and/or to stop after a predetermined amount of fluid is extracted. In addition or alternatively, the controller 62 may operate the pump, vacuum source, valve, and/or other components of the system 6 periodically or otherwise intermittently, e.g., to allow reaccumulation of fluid within the lymphatic vessels.

For example, as shown in FIG. 5, an infusion catheter 70 may be provided that includes a proximal end 70a coupled to the storage container 68, and a distal end 70b sized for delivering the stored fluid into the patient's body 90. Alternatively, the lymphatic fluid removed from the patient's body may be reinfused, e.g., after separation, treatment, and the like, back into the thoracic duct 94 using the catheter 10 already positioned in the thoracic duct 94. In addition or alternatively, the catheter 10 may be used to infuse other fluid directly into the thoracic duct 94, e.g., as described further elsewhere herein. In a further alternative, the infusion catheter 70 may be used to deliver fluid into another patient's body, e.g., such that lymphatic fluid may be removed from an organ donor's body and introduced into an organ recipient's body, e.g., after analyzing, filtering, treating, and/or otherwise manipulating the fluid, as described elsewhere herein.

In an exemplary embodiment, the catheter 10 of FIGS. 1-2B may include a single infusion lumen, e.g., for removing lymphatic fluid and returning any desired fluids back into the patient's body. Alternatively, the catheter 10 may include multiple lumens (not shown), e.g., an aspiration lumen for removing lymphatic fluid and an infusion lumen for delivering fluids (e.g., to the thoracic duct and/or adjacent vein), such as treated lymphatic fluid and/or other diagnostic or therapeutic compounds. Such lumens may terminate at the distal portion of the catheter 30 and/or more proximally. For example, the aspiration lumen may include an inlet distally beyond the balloon, e.g., for aspirating fluid from the isolated thoracic duct, while the infusion lumen may include an outlet proximal to the balloon, e.g., to provide a fluid channel into the venous system adjacent to the thoracic duct. In addition or alternatively, the catheter 10 may include a working lumen sized for receiving auxiliary devices therethrough (not shown), e.g., larger than the infusion lumen(s) for receiving one or more guidewires, auxiliary catheters, and the like (not shown). If the catheter 10 includes one or more balloons, e.g., balloon 50 shown in FIG. 1, the catheter 10 may also include one or more inflation lumens (not shown), e.g., adjacent the aspiration, infusion, and/or working lumen(s), for inflating and/or collapsing the balloon(s) together or independently of one another, as described elsewhere herein.

The catheters, systems, and methods described herein may be used to perform a variety of procedures within a patient's body, e.g., involving accessing the thoracic duct, removing lymphatic fluid from the thoracic duct, and/or infusing or reinfusing fluids into the thoracic duct. For example, during an organ explantation, a catheter, which may be any other embodiments described herein or in the applications incorporated by reference, may be introduced into the organ donor's body and directed into the donor's thoracic duct prior to organ harvest. Optionally, any of the catheters described herein may be surgically implanted into the donor body, e.g., since the donor is typically brain dead, to provide a drain or access port that has a proximal end disposed outside the donor's body, and a distal end positioned within the thoracic duct. Thus, such an implanted catheter may allow access indefinitely as needed from outside the patient's body, thereby providing access to the thoracic duct at any time during organ harvesting, e.g., to perform one or more of the procedures described elsewhere herein.

Whether introduced temporarily or surgically implanted, such a catheter may be used to remove lymph substantially continuously or intermittently, as desired. In addition, the rate of fluid removal may be adjusted, e.g. via a flow control valve, vacuum assist, or other controller outside the donor body (not shown), as described elsewhere herein and in the applications incorporated by reference. Further, the rate of flow may be controlled independent of venous pressure.

For example, as previously noted, with respect to the lungs, it is generally desirable that the lung tissue be minimally edematous with as little fluid as possible in the airspaces. Thus, once the distal end of the catheter is positioned within the thoracic duct, lymph may be substantially continuously drained in order to avoid accumulation of fluid in or around the lung, even before any clinical or physiologic indicator or pulmonary edema is evident.

Alternatively, lymph drainage may be adjusted, i.e., drained intermittently and/or at a variable flow rate, according to various clinical or physiologic indicators. For example, drainage may be increased in response to changes in oxygenation, oxygen saturation, partial pressure of oxygen in blood, or other indicators of poor ventilation or tissue perfusion. Other indicators of pulmonary edema may include findings based on chest x-ray, CT-scan, and/or other imaging modalities.

Further, the natural flow of lymph and/or pressure within the thoracic duct may be monitored and used itself as a physiologic indicator. For example, as pump function of the heart diminishes, the patient may become significantly volume overloaded, membrane permeability in the lung may increase, and/or lymphatic flow and/or pressure may change. Based on these findings, the clinician may infer that detrimental changes are occurring in the lung or other organ system and take appropriate action. For example, the outflow of lymph may be further augmented to avoid fluid accumulation. The fluid status of the patient may be manipulated, e.g., by infusion of crystalloid and/or colloid, by inducing diuresis, and the like. In addition or alternatively, cardiovascular function may be manipulated, e.g., by administration of one or more of vasopressors or vasodilators, inotropic agents, and the like.

Respiratory support may also be manipulated in response to characteristics of thoracic duct output. As an example, if the patient is ventilated, airway pressure (e.g., PEEP, etc.) may be increased, e.g., to decrease the accumulation of fluid in the airspaces of the lungs. Such modification of ventilatory parameters may be in response to changes in response to lymphatic duct flow and/or pressure. As a further example, where airway pressure is increased to decrease accumulation of fluid in the airspaces, the pressure may be increased until peak lymph flow is achieve, or, for example, until the curve representing lymph flow/pressure as a function of ventilatory pressure reaches an optimal value. This may be used to titrate ventilatory pressure to optimal effect while minimizing barotrauma.

In addition to or instead of flow and/or pressure, other parameters of lymphatic fluid may be monitored and/or manipulated using a catheter positioned in the thoracic duct, such as cell content, presence of inflammatory mediators, and may be used diagnostically and/or for therapeutic purposes.

In another embodiment, it may be desirable to preferentially drain lymphatic fluid originating from one or more organs or regions of the body. For example, in the setting of organ transplant, it is generally desirable for the lungs and/or heart to be substantially free of edema (i.e., "dry") while the liver, bowel, and kidneys may tolerate an edematous (i.e., "wet") state. Thus, a catheter may be positioned within the thoracic duct to selectively drain the lymphatics originating from a desired region, e.g., the region above the patient's diaphragm rather than the region below the diaphragm.

In an exemplary embodiment, a distal end of a catheter may be introduced retrograde into the thoracic duct toward and/or into one or more tributaries originating above the diaphragm. Alternatively, an expandable member on the catheter may be expanded to substantially isolate a region of the thoracic duct, e.g., the region above the diaphragm from the region below the diaphragm. Fluid may then be removed from the region above or proximal to the expandable member using the catheter. In another alternative, a large volume of lymph may be drained quickly from the thoracic duct using a catheter to deplete the capacitance of the lymphatics in close proximity to the thoracic duct, e.g., those above the diaphragm after which the thoracic system may be allowed to re-equilibrate.

In still another embodiment, it may be desirable to identify the lymphatics, for example, so that they may be treated appropriately during a surgical procedure, (e.g., identified, avoided, dissected, cannulated, reconnected, and the like). For example, in the setting of lung transplant, the lymphatics are generally ignored during conventional explantation of the organ and reimplantation. However, if the lymphatics can be readily identified, it may be beneficial to ensure that drainage is maintained within a donor body or a recipient body, at least temporarily post-transplant.

In an exemplary embodiment, this may be accomplished by positioning a distal end of a catheter (and the one or more inlet ports thereon) within the thoracic duct in or around the area of the hylar lymphatic vessels and/or hylar lymph nodes. Such a drainage catheter may be placed at the time of explant or implant and left in place indefinitely to drain fluid, cells, inflammatory mediators, and/or other components of lymph.

In an alternative embodiment, identification of the lymphatic channels may assist in reconnecting channels at the time of implantation. For example, a catheter positioned within the thoracic duct of the recipient body may facilitate identifying the lymphatic vessels and/or lymph nodes, e.g., by infusing one or more of a dye (e.g., colored, fluorescing, and the like), contrast agent, and/or other marker, or by retrograde introduction of a device, e.g., Guidewire (not shown) through the lymphatics.

In addition to or instead of monitoring and manipulating fluid volumes and pressures, access to the lymphatic system may enable monitoring and manipulating other lymphatic contents including cells and mediators of inflammatory response. For example, again in the setting of transplant, the presence of donor cells, especially T-cell and macrophages, may result in an undesirable response in the organ transplant recipient, e.g., graft-versus-host-disease ("GVHD"). Thus, depletion of such undesired cells from the donor and/or donor organs before transplant may be beneficial and improve outcomes.

In an exemplary embodiment, a catheter (again such as any of the embodiments described herein or in the applications incorporated by reference) may be positioned within the thoracic duct of a potential donor body and lymph may be removed for the purpose of removing potentially detrimental cells and/or mediators. The output of the catheter may be filtered, sorted, or otherwise manipulated, and a sub-component may be discarded while one or more other components may be reintroduced back into the donor body, e.g., via the catheter or another infusion device. For example, cells and/or inflammatory mediators may be removed and the remaining fluid and/or other contents may be reinfused, or vice versa.

In combination with this approach, one or more agents may be administered to the donor to mobilize cells of interest, e.g., T-cells and macrophages, and at least transiently increase their concentration in lymph, thus facilitating more rapid removal. As discussed elsewhere, a catheter may be positioned within or around the lymphatics of the donor and remain in place post-transplant, e.g., to continue elimination of deleterious components of lymph for some period after the transplantation procedure. For example, such a catheter may facilitate the washout of T-cells, macrophages, or other contributors to the development of GVHD.

In still another embodiment, a catheter may be positioned within the thoracic duct of a potential donor or recipient to sample lymph for the purpose of screening for viability as a donor and/or matching/establishing compatibly with a potential recipient. For example, donor matching, HLA typing, and the like is usually performed on peripheral blood. However, lymph contains a much higher concentration of immune cells and therefore may provide a more detailed evaluation of cell surface markers and/or other parameters by which compatibility of the donor and recipient may be established.

In another embodiment, post-transplant, a catheter may be positioned within the thoracic duct of an organ recipient to cannulate and/or drain the thoracic duct, e.g., to substantially deplete immune cells and/or mediators of the donor that are resident in the graft and may migrate selectively into the recipient lymphatic system, e.g., T-cells, macrophages, other immune cells, immune and inflammatory mediators, and the like.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A method for harvesting one or more organs from a donor body, comprising:
   introducing a distal end of a tubular member into a vasculature of the donor body;
   introducing the distal end of the tubular member into a thoracic duct of the donor body;
   removing fluid from the thoracic duct via the tubular member to a location exterior to the donor body to control fluid accumulation within or around the one or more organs before removing the one or more organs from the donor body; and
   removing the one or more organs from the donor body.

2. The method of claim 1, wherein the one or more organs comprises a lung, and wherein fluid is removed from the thoracic duct to minimize edema in the lung before removing the lung from the donor body.

3. The method of claim 2, wherein removing fluid from the thoracic duct further comprises adjusting an amount of fluid removed from the thoracic duct based on one or more physiologic indicators of the donor body reflecting changes in edema within the lung.

4. The method of claim 3, wherein removing fluid from the thoracic duct further comprises monitoring the one or more physiologic indicators of the donor body comprising one or more of: a) oxygenation or oxygen saturation within the donor body, b) pressure of oxygen within blood in the donor body, c) imaging the donor body.

5. The method of claim 1, wherein fluid is removed from the thoracic duct substantially continuously until the one or more organs are removed from the donor body.

6. The method of claim 1, wherein removing fluid from the thoracic duct comprises:
   monitoring one or more parameters of fluid within the thoracic duct; and
   increasing a rate of fluid removal to avoid fluid accumulation within the one or more organs.

7. The method of claim 6, wherein the one or more parameters comprise one or more of: a) flow rate of fluid into the thoracic duct, and b) pressure within the thoracic duct.

8. The method of claim 1, further comprising infusing one or more compounds into the thoracic duct via the tubular member.

9. The method of claim 8, wherein the one or more compounds comprise one or more of: a) a crystralloid or a colloid, b) a vasopressor, c) a vasodilator, and d) an inotropic agent.

10. The method of claim 8, wherein the one or more compounds are introduced into the thoracic duct to induce diuresis of the donor body.

11. The method of claim 1, wherein removing fluid from the thoracic duct comprises preferentially draining fluid from a region of the thoracic duct originating from the one or more organs.

12. The method of claim 11, wherein the one or more organs comprises a lung, and wherein the region comprises a region of the thoracic duct adjacent at least one of hylar lymphatic vessels of the donor body and hylar lymph nodes of the donor body.

13. The method of claim 1, wherein introducing the distal end of the tubular member into the thoracic duct comprises:
   positioning an expandable member on the distal end of the tubular member at a desired location within the thoracic duct;
   expanding the expandable member to substantially isolate a distal region of the thoracic duct distally beyond the expandable member from a proximal region of the thoracic duct proximal to the expandable member; and
   wherein removing fluid from the thoracic duct comprises removing fluid from one of the proximal region and the distal region.

14. The method of claim 13, wherein the desired location is aligned with a diaphragm of the donor body, and wherein removing fluid from the thoracic duct comprises removing fluid from the proximal region of the thoracic duct above the diaphragm.

15. The method of claim 1, wherein introducing the distal end of the tubular member into the thoracic duct comprises:

introducing the distal end from the thoracic duct into a tributary vessel communicating with the one or more organs.

16. The method of claim 1, further comprising removing fluid from the thoracic duct via the tubular member after removing the one or more organs from the donor body.

17. The method of claim 1, wherein fluid is removed from the thoracic duct to remove one or more donor cells from the one or more organs to reduce graft-versus-host-disease (GVHD) in a recipient receiving the one or more organs.

18. The method of claim 17, further comprising:
separating the one or more donor cells from the fluid removed from the thoracic duct;
and introducing one or more components of the removed fluid back into the donor body.

19. The method of claim 17, further comprising administering one or more agents into the donor body to enhance mobilization of the one or more donor cells into the thoracic duct.

20. The method of claim 17, wherein the fluid is removed to reduce at least one of T-cells and macrophages from the one or more organs before being removed from the donor body.

21. A method for harvesting one or more organs from a donor body, comprising:
introducing a distal end of a tubular member into a thoracic duct of the donor body;
removing fluid substantially continuously or intermittently from the thoracic duct via the tubular member to a location exterior to the donor body to control fluid accumulation within or around the one or more organs before removing the one or more organs from the donor body; and
removing the one or more organs from the donor body.

22. The method of claim 21, wherein the one or more organs comprise a lung, and wherein the fluid is removed in order to avoid accumulation of fluid in or around the lung before removing the lung from the organ body.

23. The method of claim 22, wherein removing fluid comprises adjusting an amount of fluid removed from the thoracic duct based on one or more physiologic indicators of the donor body reflecting changes in edema within the lung.

24. The method of claim 21, wherein the tubular member is surgically implanted into the donor body with the distal end introduced into the thoracic duct.

* * * * *